(12) United States Patent
Schlumberger

(10) Patent No.: US 6,431,745 B1
(45) Date of Patent: Aug. 13, 2002

(54) DEVICE AND METHOD FOR MIXING AND WASHING LIQUIDS AND/OR SOLIDS AND FOR WASHING CONTAINERS

(75) Inventor: Helmut Schlumberger, Polling (DE)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 09/674,257
(22) PCT Filed: Apr. 28, 1999
(86) PCT No.: PCT/EP99/02859
§ 371 (c)(1), (2), (4) Date: Mar. 20, 2001
(87) PCT Pub. No.: WO99/56863
PCT Pub. Date: Nov. 11, 1999

(30) Foreign Application Priority Data

Apr. 30, 1998 (DE) .......................... 198 19 447

(51) Int. Cl.$^7$ ................................ B01F 11/00
(52) U.S. Cl. ........................................ 366/211
(58) Field of Search ............... 366/208–211, 213–216, 366/219, 237, 348, 601

(56) References Cited

U.S. PATENT DOCUMENTS

| | | | |
|---|---|---|---|
| 2,516,655 A | * | 7/1950 | Smith |
| 2,545,914 A | | 3/1951 | Boucher |
| 3,116,744 A | | 1/1964 | Hager |
| 3,163,404 A | * | 12/1964 | Kraft et al. |
| 3,614,434 A | * | 10/1971 | Horwitz |
| 3,711,379 A | * | 1/1973 | Adams |
| 4,479,720 A | * | 10/1984 | Mochida et al. |
| 5,261,742 A | | 11/1993 | Lockhart |
| 5,499,872 A | * | 3/1996 | Baxter |
| 5,580,524 A | * | 12/1996 | Forrest et al. |
| 5,697,701 A | * | 12/1997 | Forrest et al. |
| 6,238,330 B1 | * | 5/2001 | Marziali |

FOREIGN PATENT DOCUMENTS

| | | |
|---|---|---|
| EP | 0 329 183 A3 | 8/1989 |
| EP | 0 435 481 A2 | 7/1991 |
| EP | 0 465 285 A2 | 1/1992 |
| EP | 0 421 985 B1 | 4/1992 |
| GB | 2 081 118 A | 2/1982 |
| WO | WO 91/15768 | 10/1991 |
| WO | WO 97/11375 | 3/1997 |
| WO | WO 97/16240 | 5/1997 |

* cited by examiner

Primary Examiner—Charles E. Cooley
(74) Attorney, Agent, or Firm—Pennie & Edmonds LLP

(57) ABSTRACT

A holder containing a mixing vessel is rotatable about its longitudinal axis by a drive configured to rotate the holder alternately in a clockwise and anti-clockwise direction. A programmable control unit is configured to regulate an angular excursion (α) of the holder in the clockwise and anti-clockwise direction. The control unit includes instructions for a mixing sequence to be carried out in which the holder carries out first angular excursions of a first angle in a first cycle and second angular excursions of a second angle in a second cycle. The process includes placing liquids and/or solids into the mixing vessel, and then inserting the mixing vessel into the holder. The holder is subsequently alternately rotated by the drive through the first angular excursions and then the second angular excursions.

17 Claims, 3 Drawing Sheets

360° rotation in a period of 100ms torus formation secondary flow (circular flow)

primary flow (circular flow)

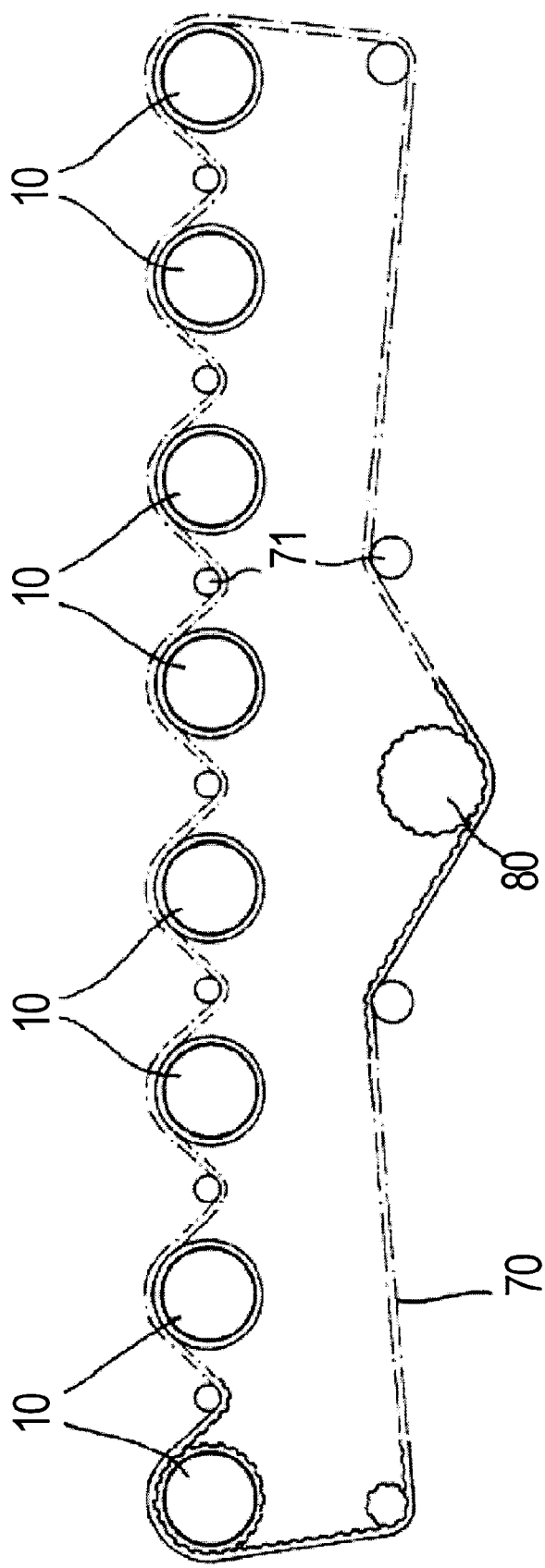

US 6,431,745 B1

DEVICE AND METHOD FOR MIXING AND WASHING LIQUIDS AND/OR SOLIDS AND FOR WASHING CONTAINERS

This invention claims priority to German patent application no. 198 19 447.1 filed on Apr. 30, 1998, and PCT application Ser. No. PCT/EP99/02859 filed on Apr. 28, 1999.

BACKGROUND OF THE INVENTION

1. Field of the Invention

The present invention is in the field of mixing and washing liquids and/or solids. In particular the present invention concerns non-invasive mixing and washing processes which involve relatively highly viscous liquids.

The present invention concerns a device for mixing liquids and/or solids comprising
- a holder for a mixing vessel which is rotatably mounted such that a mixing vessel located in the holder can be rotated about its longitudinal axis,
- a drive which can rotate the holder alternately in a clockwise and anti-clockwise direction,
- a programmable control unit which regulates the angular excursion of the holder in a clockwise and anti-clockwise direction and in which the angular excursion is stored.

2. Description of Related Art

Many mixing methods are known in the prior art such as invasive mixing methods in which a stirrer or such like is immersed in a vessel containing the substances to be mixed. Such invasive mixing methods are disadvantageous especially in the analytical field since the stirrer can cause contamination and carry-over. Hence in the analytical field non-invasive mixing methods such as vortex mixing are preferred. In this type of mixing, a vessel with its contents is set in motion. The motion can for example be a simple backwards and forwards oscillation but usually the vessel movements are in the shape of an eight or other Lissajou's figures. However, a disadvantage of vortex mixing is the relatively strong vibrations that it causes and the risk of aerosol formation.

Other mixing methods are known in the prior art in which a vessel is rotated about its longitudinal axis in order to mix the liquids and/or solids that are contained therein. For example an apparatus is described in WO 91/15768 in which sample vessels are arranged eccentrically on a motor axis and are rotated by the motor alternately in a clockwise and anti-clockwise direction. Another device is described in U.S. Pat. No. 5,580,524 in which rotatably mounted vessels are rotated by contacting the external surface of the vessels with a rotating disk. This document describes that reversing the direction of rotation can suspend magnetic particles in a liquid.

BRIEF SUMMARY OF THE INVENTION

The apparatuses described in the documents WO 91/15768 and U.S. Pat. No. 5,580,524 have the disadvantage that the washing and mixing cannot be adapted to the specific circumstances of the respective vessel content. No information is given in these documents about the possibility of adapting the rotation process in order to optimize the results. In contrast the present invention has the advantage that by changing the mixing process it is possible to achieve a considerable improvement in the mixing efficiency. In particular the present invention allows the use of mixing sequences in which two or more different mixing processes are combined. It has been experimentally demonstrated that the use of such mixing sequences greatly increases the mixing efficiency. A further advantage of apparatuses and methods according to the invention is that they effectively prevent splashing and aerosol formation. Furthermore the invention enables the meniscus deflection to be kept small such that mixing is also possible in almost completely filled vessels without a closure.

BRIEF DESCRIPTION OF THE DRAWINGS

Additional objects and features of the invention will be more readily apparent from the following detailed description and appended claims when taken in conjunction with the drawings, in which:

FIG. 4 shows a device for simultaneous mixing in a plurality of sample vessels.

Like reference numerals refer to corresponding elements throughout the several drawings.

DESCRIPTION OF THE PREFERRED EMBODIMENTS

Figure 1:
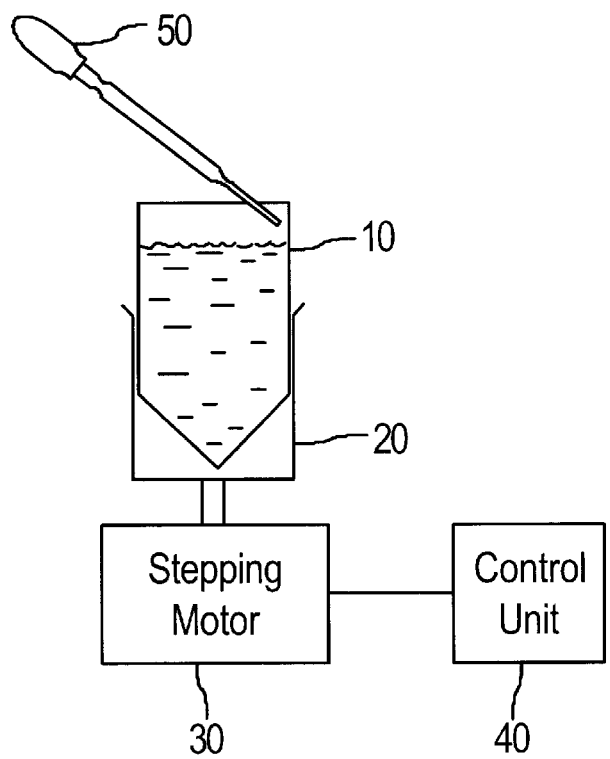
FIG. 1 shows schematically a mixing device according to the invention.

The field of application of the present invention is, as already mentioned, primarily in the field of analysis where contamination by carry-over or such like must be avoided. Within the sense of the invention, the analytical field should also encompass processes which precede the actual analysis such as dilution, lysis or transfer of sample material. The mixing process according to the invention can for example be used to mix together two or more liquids. This is particularly important when one of the liquids to be mixed has a high viscosity such is the case for blood, serum, samples containing nucleic acids and also oils etc. Additional important field of application or the present invention is the suspension of particles in a liquid in order to wash the particles or to efficiently contact them with constituents of the liquid. Particles are washed with liquid by mixing particles and liquid. Such processes have become very important in the field of analysis using magnetic particles. The invention can also be used to wash the inner wall of vessels.

In order to carry out a mixing process or washing process using a device according to the invention, the liquids and/or solids are firstly added to a mixing vessel. A particular advantage of the present invention is that the mixing vessel does not have to meet particular requirements. On the contrary it is possible to use standard laboratory test tubes, centrifuge tubes, Eppendorf tubes etc. Preferred vessel volumes are between 0.05 and 5 ml. However, if the drive is appropriately dimensioned it is also possible to mix substantially larger volumes. Rotationally symmetrical vessels are preferably used. The process according to the invention allows mixing in vessels that are open at the top without the danger of splashing, aerosol formation etc.

A person skilled in the art knows the practical problems which occur when a solid that has sedimented at the bottom of a vessel has to be suspended or dissolved. The problem is particularly severe when the mixing vessel has a tapered bottom. It has been shown that the present invention achieves a very rapid suspension of a sedimented solid even when the mixing vessel has a tapered bottom.

The mixing vessels that are used can have a round inner cross-section which has no projecting parts or such like. On the other hand it can also be advantageous to provide projecting parts within the vessel which act as so-called baffles and intensify the mixing process. However, according to the invention it is important that projecting parts or edges in the interior of the vessel are below the liquid surface since projecting parts or edges in the area of the liquid interface can lead to a splashing of liquid when the vessel is rotated according to the invention alternately in a clockwise and anti-clockwise direction. It has turned out that the distance between the projecting parts or edges and the liquid surface should be one or a few millimeters. The necessary distance is determined by a number of factors such as the type of liquid, speed of the angular excursion and the size of the baffle.

It has proven to be particularly advantageous to use vessels in which the lower part of the vessel has a polygonal cross-section (in particular quadrangular, hexangular and octangular) and the upper region of the vessel has a round inner cross-section. The dimensions of the vessel and the liquid volume are selected such that the liquid surface is in the circular cross-sectional region. Such vessels not only facilitate the mixing process, they can also be used as cuvettes. In particular with a quadrangular cross-section of the lower part of the vessel, it is possible to use opposite sides to transmit radiation through the vessel. Hence such a vessel can be used to carry out mixing, suspensions, reactions and a subsequent analysis.

A device according to the invention can also operate with mixing vessels that do not have a typical tube shape. It has turned out that in a borderline case it is even possible to use a planar hydrophobic surface on which a volume of liquid is applied. In order to carry out the mixing process, the surface is rotated about an axis which is essentially perpendicular to the surface and which passes through the coherent liquid volume. Hence the axis is advantageously selected such that it passes through the centre of gravity of the liquid volume. It has proven to be particularly advantageous to use a small cup (dimensions e.g. diameter 0.7 cm; depth 0.3 cm) as the mixing vessel. Such a mixing vessel has the advantage compared to a surface that no interfering spreading of liquid can take place and the ideal axis or rotation is already defined. In particular such cups allow a procedure in which immunological binding takes place on the inner side of the cup and excess binding partner is separated in washing step. Washing away excess binding partner from the inner side of the cup or generally from the inner side of the vessel can be advantageously carried out with the inventive method. It has turned out that this type of cleaning of the inner side of the vessel is very efficient and non-destructive i.e. immunological binding to the surface remains intact.

Correspondingly methods for washing vessels are also part of the present invention in which the vessel is in a holder and the inner wall of the vessel is washed by alternately rotating the vessel containing a liquid that is present in the vessel. The ability to adjust the angular excursion of the alternating rotation according to the invention enables the wash process to be adapted to the respective requirements. The liquid required to wash the inner wall of the vessel can be added to the vessel before starting the alternating rotation. However, it has also turned out to be advantageous to dispense the liquid on the inner vessel wall using a pipette 50 (FIG. 1) while the vessel is alternately rotated. Such a washing process can in principle be used for any vessels, but it has turned out to be advantageous to use the process to wash the inner wall of vessels where at least a part of the inner wall of the vessels is coated immunologically or with a nucleic acid sequence.

A mixing device according to the invention has a holder for a mixing vessel, a drive which rotates the holder and a control unit which regulates the movement of the drive. The holder is used to hold the mixing vessel. For example in order to hold a cylindrical mixing vessel, the holder can also be a cylinder of such a size that the mixing vessel can be inserted into it and the walls of the mixing vessel and holder sit closely together. In addition holders are possible which have holding devices to secure the vessel. Such holding devices can for example be gripping jaws with a variable distance between them in order to receive vessels of different sizes. It is desirable to construct the holder such that it is symmetrical about an axis in order to avoid imbalance during the mixing process. In addition the holder should be designed such that the mixing vessel is held in the middle and the axis of the holder and the axis of the mixing vessel are as far as possible coincident.

The holder is set in alternating rotation by a drive. The maximum rotation of the holder from its resting position before it begins to turn in the opposite direction is referred to as the angular excursion ($\alpha$) in the invention.

For the alternating rotation the holder can for example be mounted directly on the spindle of a motor or it can be rotatably mounted on a support and driven by a belt or such like. Embodiments are also possible which are based on the apparatus described in U.S. Pat. No. 5,580,524. In such embodiments a rotatably mounted holder is achieved by coupling a motor to a gear ring or to a circular external peripheral surface of the holder.

The drive can be operated by a conventional analogue motor, a stepping motor, Piezo motor etc. The dimensions of the drive motors depend on the moment of inertia of the holder and the filled mixing vessel. A further criterium that the motors should fulfil is that their angular excursion is reproducible when regulated suitably in order to achieve reproducible mixing conditions. This is of course the case for stepping motors but it also turned out that the angular excursion of simple analogue motors can be regulated accurately enough during the alternating rotation.

Drives can also be used in the invention which simultaneously rotate two or more holders. An example of such a drive is shown in FIG. 5b of U.S. Pat. No. 5,580,524. Another possibility for such a multi-drive is described further below in this application.

An important feature of the present invention is the control unit and the way it operates. A commercially available control card which controls the stepping motor according to an input sequence can be used as a control unit for stepping motors. Such combinations of control card and stepping motor are offered as a set. The control cards are usually designed such that they can be directly connected to the standardized interfaces of computers. A suitable combination of stepping motor and control card that can be used to carry out the present invention is for example obtainable from the Motion Company under the name FOS-motor controller.

Analogue motors can be controlled by a circuit which yields a voltage-time profile. Possible voltage profiles are for example sinus, square or saw-tooth curves. The angular excursion (α) can be determined experimentally for a given motor using different voltage-time curves. Preferably a signal such as a sinus, square wave or delta voltage is used for this which has essentially two adjustable variables i.e. the amplitude and period. The desired angular excursions of the holder can be achieved by varying these two parameters. It is for example possible to store the parameters that have been determined for particular angular excursions in the form of a table so that when a certain angular excursion is desired it is possible to utilize the appropriate voltage-time course. If a suitable value has been selected for one of the two parameters then it is possible to control the variation of the angle over a wide range by using the second parameter. In this manner it is for example possible to construct a very simple mixing device in which the angular excursion can be changed by means of a single manually operated adjuster. Such an adjuster can for example be a potentiometer which adjusts the amplitude of the above-mentioned voltage-time profiles.

A further important quantity which influences the mixing process is the time required for an annular excursion. The angular excursion divided by this time gives an averaged angular velocity of the holder. This velocity together with the angular excursion is of pivotal importance for the mixing effect. This is elucidated further in connection with the experimental observations.

It has in addition turned out that the number of rotations of the holder in a clockwise and anti-clockwise direction is important for the result of the mixing process. Hence provision is made for programming the number of angular excursions in order to achieve reproducible mixing results. In addition it is advantageous when the control unit has a storage unit in which process parameters such as angular excursion, number of excursions etc. can be stored. It is also possible to connect the control unit to a reading instrument for bar codes, magnetic strips, punch cards etc. in order to read-in the relevant data for the process parameters.

Within the scope of the invention it has also proven to be particularly advantageous to alternate between mixing cycles with a first angular excursion and cycles with a second angular excursion. This fact is also discussed in more detail in connection with experimental observations.

FIG. 1 shows schematically a mixing device according to the invention. A mixing vessel (10) is located in the holder (20). In the example shown, the holder is a plastic casing which tightly surrounds the mixing vessel (10). The lower end of the plastic casing is closed with a plastic plug into which the spindle of a stepping motor (30) is recessed. The stepping motor (30) is regulated by a control unit (40). The control unit comprises a control card for the stepping motor and a computer into which the control card is inserted. The software for the control card enables programs to be created which exactly describe the time course and rotation of the stepping motor (30).

Figure 2:
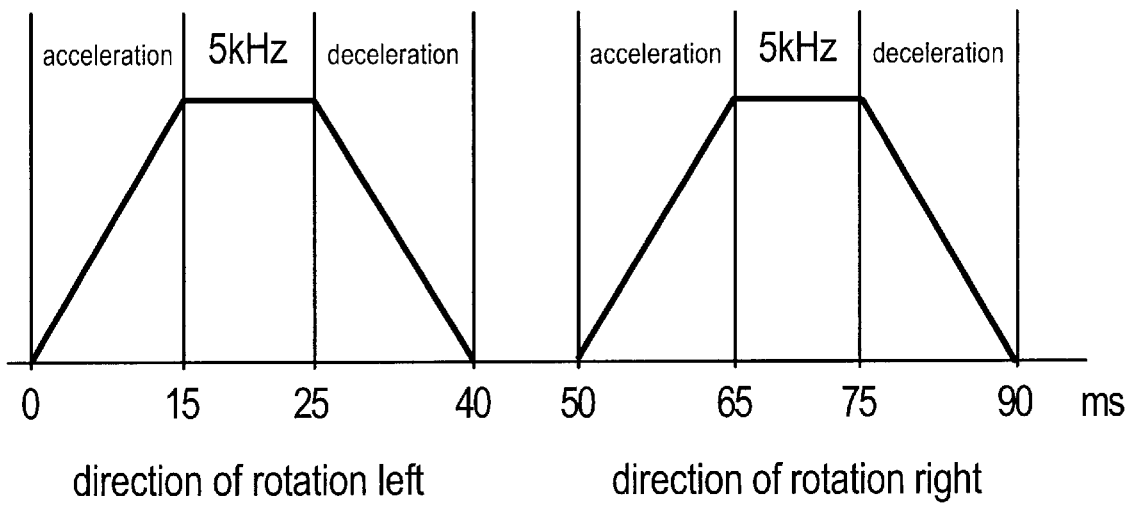
FIG. 2 shows an example of the control of a stepping motor.

FIG. 2 shows an example of the control of a stepping motor. The time in milliseconds is plotted on the X axis and the stepping frequency of the stepping motor is plotted on the Y axis. The angular excursion of the stepping motor is 3.6°/step and hence on the plateau labelled 5 kHz in FIG. 2, a velocity of 50 revolutions per sec is achieved. Starting up the stepping motor by means of a ramp as shown in FIG. 2 is only necessary to protect the motor. In order to carry out the mixing process according to the invention, care must only be taken that the acceleration of the mixing vessel is not so abrupt that splashing occurs.

Figure 3D:
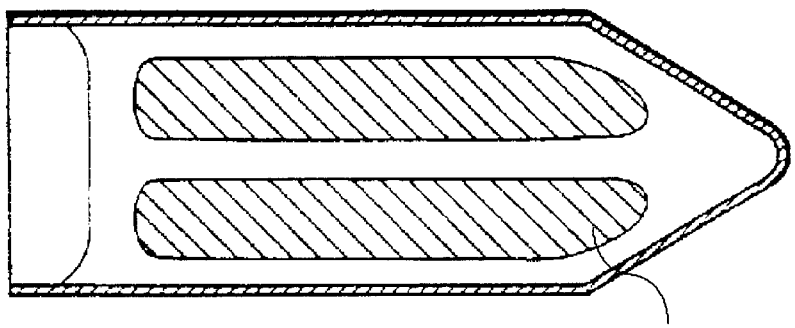
FIGS. 3C and 3D are cross sectional views similar to that shown in FIG. 3B, but show different mixing flows.
Figure 3C:
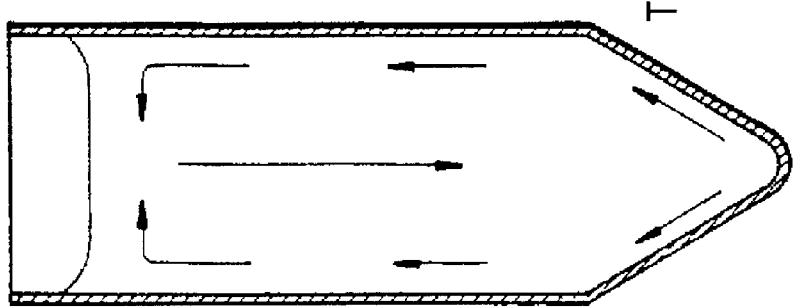
Figure 3B:
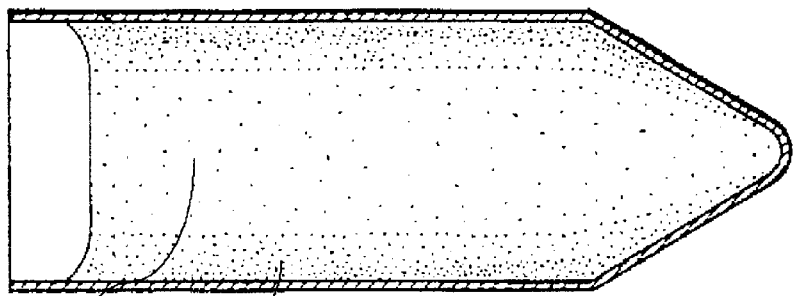
FIG. 3B is cross sectional view taken along line 3B–3B' of FIG. 3A showing a side view of the mixing flow depicted in FIG. 3A.
Figure 3A:
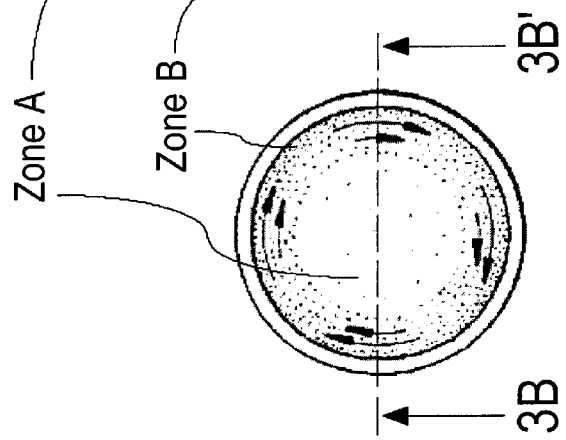
FIG. 3A is a plan view of a mixing vessel showing an example of a mixing flow that is obtained using the mixing device shown in FIG. 1.

Examples of flow diagrams are shown in FIGS. 3A to 3D that are obtained with an arrangement according to FIG. 1. When the mixing vessel is rotated about its longitudinal axis, a primary flow firstly occurs in the form of a circular flow (FIG. 3A). This flow is caused by the inertia of the vessel contents and the shear forces between the liquid and wall resulting from the vessel rotation. The velocity of the circular flow decreases rapidly from the wall towards the vessel axis. As a result of the deflected flow and the centripetal force, a secondary flow is generated in the form of a vertical flow as shown schematically in FIG. 3B. Depending on the shape of the bottom of the vessel, this secondary flow is oriented such that it ascends at the vessel wall and descends near to the vessel axis. The velocity of the secondary flow is largest in the area of the vessel wall and of the vessel axis as well as at the bottom and surface of the liquid. In the intermediate regions the secondary flow is relatively small so that none or only a slight mixing occurs in these regions. FIG. 3C shows the result of an alternating angular excursion (680 degrees in 160 ms) which was obtained using a coloured heavy liquid (glycerol) which was covered with a layer of colourless lighter liquid (water). FIG. 3D shows that a torus of unmixed liquid is formed which can only be mixed after a very long period of alternating rotation. By changing the angular excursion, in this case by reducing the angular excursion, it is possible to mix the unmixed region with the remaining liquid. The transition to another angular excursion and thus the change in angular velocity also changes the primary flow and the torus can at least be partly broken since there is a shift in those regions of liquid that are substantially at rest. It is preferred according to the invention to alternate between rotation cycles with a first angular excursion and rotation cycle with a second angular excursion in order to avoid formation of unmixed regions and to efficient mixing.

The following table gives characteristic data for a mixing process according to the invention in which alternating cycles of angular excursions of different dimensions were used. In this example 1 ml glycerol (50%) was overlaid with 0.5 ml isopropanol which was previously stained wit methylene blue in a conical vessel with an inner diameter of 10 mm. This type of in which a highly viscous liquid is located below a liquid of low viscosity is very demanding on a mixing process. Mixing to the point of visually detectable homogeneity was already achieved after step 4 of the table shown below using the device according to FIG. 1.

| Step | Time for an angular excursion in ms | Angle in degree | Number of cycles |
| --- | --- | --- | --- |
| 1 | 90 | 270 | 15 |
| 2 | 45 | 60 | 10 |
| 3 | 90 | 270 | 15 |
| 4 | 45 | 60 | 10 |
| 5 | 90 | 270 | 15 |
| 6 | 45 | 60 | 10 |
| 7 | 90 | 270 | 10 |

With the mixing process using the above-mentioned sequence, a secondary flow is firstly generated with large angular excursions of 270° which results in the formation of a torus of coloured isopropanol. The cycles with an angular excursion of 60° radially mixes the liquid located in the torus with the adjacent liquid.

In order to better demonstrate the advantages of this mixing process, the results of three other types of mixing cycles are shown in the following table:

| Example No. | Time/ms | Angle/° | Number of cycles | Mixing result |
|---|---|---|---|---|
| 1 | 70 | 180 | 20 | Liquids segregate when the vessel stands still. |
| 2 | 95 | 270 | 20 | Vortex almost reaches the bottom, however, there is again a complete de-mixing when the vessel is at a standstill. |
| 3 | 100 | 360 | 20 | Long vortex reaching the bottom, but mixing is incomplete. |

The optimal conditions for a given mixing problem can be found with the following procedure:

1. The angular excursion is slowly increased starting at for example 180° until the vortex that forms almost reaches the bottom or until a maximum allowable meniscus deflection is reached.
2. It is checked how many cycles are necessary with the angle found in step 1 to allow a torus to form. Usually the number of cycles that are necessary is between 10 and 25.
3. A cycle with short angular excursions is added to a cycle defined according to the parameters found in steps 1 and 2. The short angular excursions should be selected between 40 and 100°. It is then observed how many cycles are necessary in order to mix the torus formed in step 2 with the surrounding liquid.
4. Depending on the desired homogeneity of the mixture additional cycles with long and short angular excursions are added alternately to the two described cycles.

For automated instruments under laboratory conditions it will usually not be possible to optimally adapt the mixing process to the respective samples since the properties of the sample differ from one another. A mixing process that takes into account the numerous mixing problems that occur in practice has parameters in the following ranges:

First cycle: angular excursion in the range of 80 to 1500°; 3 to 30 cycles

Second cycle: angular excursion in the range of preferably 10 to 180°; 3 to 30 cycles The angular excursion in the second cycle is selected to be smaller than in the first cycle in order to disintegrate the torus that forms.

Cycles 1 and 2 are carried out successively. Such a sequence comprising a cycle with a large angular excursion and a cycle with a small angular excursion is referred to as a mixing sequence. Preferably two or more successive mixing sequences are carried out on a sample.

A further important application of the invention is to suspend particles and in particular magnetic particles in a liquid. It has turned out that for this solid/liquid mixing problem it is advantageous to be able to adjust the angular excursion of the holder in order to achieve optimal results. In addition a problem like that of torus formation occurs when particles are resuspended. When the vessel is rotated with a constant to and fro movement, particles collect in regions so that usually there is not a uniform distribution. Frequently such a suspension is carried out in order to bring the particles as completely as possible into contact with the liquid for example in order to bind molecules contained in the liquid to the particle surface. For suspension processes it has proven to be advantageous, like the liquid/liquid mixing, to firstly carry out a mixing cycle with excursions of a first angle and then to carry out one or several mixing cycles with other angular excursions.

It has turned out that the present invention can be used in particular to lyse or to purify nucleic acids. During these processes mixtures occur at various stages which are difficult to homogenise due to the high viscosity of liquids containing nucleic acids. In addition it has turned out that the reproducibility of nucleic acid analyses can be increased by using the mixing process according to the invention. A possible reason for this is that the (reproducible) shear forces that occur in the process according to the invention result in a detachment of the nucleic acids from the adhering proteins. In addition nucleic acid strands run the risk of being divided in the mixing process due to their length. The mixing process according to the invention results in an increased reproducibility and accuracy in analytical methods which may be due to the fact that the division of nucleic acid strands occurs more reproducibly than in other methods.

A device for simultaneous mixing in a plurality of sample vessels (10) is shown in FIG. 4. In this embodiment the sample vessels are in holders which have a toothed rim on their outer surface and are freely rotatably mounted. The holders are connected together by a circumferential toothed belt (70) and are driven by a common drive (80). In the example shown the drive is composed of a gear wheel which is mounted on the spindle of a drive motor. The motor can be regulated by the control described in FIG. 1. In order to maintain the tension of the toothed belt (70) and to ensure the toothed belt rests against the holders, deflection rollers (71) are provided in the arrangement.

What is claimed is:

1. A device for mixing liquids and/or solids or for washing solids with liquids comprising:
   a) a holder for a mixing vessel which is rotatably mounted such that a mixing vessel located in the holder can be rotated about its longitudinal axis, where the mixing vessel contains one or more liquids and/or one or more solids;
   b) a drive configured to rotate the holder alternately in a clockwise and anti-clockwise direction; and
   c) a programmable control unit configured to regulate an angular excursion ($\alpha$) of the holder in a clockwise and anti-clockwise direction,
   wherein the control unit includes instructions for a mixing sequence to be carried out in which the holder carries out first angular excursions of a first angle in a first cycle and carries out second angular excursions of a second angle in a second cycle.

2. The device as claimed in claim 1, in which the programmable control unit is configured to control the time for the first and second angular excursions.

3. The device as claimed in claim 1, in which the programmable control unit is configured to control the number of angular excursions in a clockwise and anti-clockwise direction.

4. The device as claimed in claim 1, in which the programmable control unit is connected to a keyboard or a computer for programming.

5. The device as claimed in claim 1, in which the programmable control unit is connected to a reader which is used to read in data from a data carrier in order to program the control unit.

6. The process for mixing liquids and/or solids or for washing solids with liquids comprising:

a) placing one or more liquids and/or one or more solids that are to be mixed in a mixing vessel,
b) inserting the mixing vessel in a rotatably mounted holder, and
c) alternately rotating the holder with a drive in a clockwise and an anti-clockwise direction through first angular excursions of a first angle in a first cycle and through second angular excursions of a second angle in a second cycle, where said first angle is different to said second angle.

7. The process as claimed in claim 6, further comprising controlling the time of each of the first and second angular excursions.

8. The process as claimed in claim 6, further comprising controlling the number of first and second angular excursions.

9. The process as claimed in claim 6, wherein the first angle is larger than the second angle.

10. The process as claimed in claim 6, wherein the first angle is between 80 and 1500 degrees.

11. The process as claimed in claim 6, wherein the second angle is between 10 and 180 degrees.

12. The process as claimed in claim 6, wherein the number of first angular excursions is between 1 and 30.

13. The process as claimed in claim 6, wherein the number of second angular excursions is between 1 and 30.

14. The process as claimed in claim 6, further comprising alternately rotating the holder through one or several additional angular excursions.

15. The process as claimed in claim 6, wherein the first angle is selected such that a vortex formed by the alternating angular excursions reaches near to the bottom of the mixing vessel.

16. The process as claimed in claim 6, wherein the one or more liquids are introduced while the mixing vessel is rotated alternately.

17. The process as claimed in claim 6, wherein the one or more liquids are placed in the mixing vessel with a pipette at an inner wall of the mixing vessel.

* * * * *